United States Patent
Lurz et al.

(10) Patent No.: US 6,767,512 B1
(45) Date of Patent: *Jul. 27, 2004

(54) TEMPERATURE-REGULATING BLOCK WITH TEMPERATURE-REGULATING DEVICES

(75) Inventors: Werner Lurz, Kaltenkirchen (DE); Ruediger Brust, Ziethen (DE); Dietmar Jodies, Ellerau (DE); Ernst Tennstedt, Hamburg (DE)

(73) Assignee: Eppendorf AG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,124

(22) PCT Filed: Nov. 7, 1997

(86) PCT No.: PCT/EP97/06194
§ 371 (c)(1),
(2), (4) Date: Jun. 30, 1998

(87) PCT Pub. No.: WO98/20975
PCT Pub. Date: May 22, 1998

(30) Foreign Application Priority Data

Nov. 8, 1996 (DE) .......................................... 196 46 115

(51) Int. Cl.[7] .................................................. B01L 9/00
(52) U.S. Cl. .......................... 422/104; 422/99; 422/102; 436/155; 436/157
(58) Field of Search ............................ 422/99, 64, 102, 422/104, 942; 436/47, 48, 157; 435/303.1, 288.4

(56) References Cited

U.S. PATENT DOCUMENTS

| | | | |
|---|---|---|---|
| 3,556,731 A | | 1/1971 | Martin .......................... 23/253 |
| 3,801,467 A | * | 4/1974 | Nobe et al. ................... 195/139 |
| 3,985,508 A | | 10/1976 | Williams ....................... 23/253 |
| 4,504,733 A | * | 3/1985 | Walsh .......................... 219/521 |
| 4,679,615 A | | 7/1987 | Livne ............................ 165/1 |
| 4,865,986 A | * | 9/1989 | Coy et al. .................... 435/290 |
| 4,981,801 A | * | 1/1991 | Suzuki et al. ................ 435/290 |
| 5,061,630 A | | 10/1991 | Knopf .......................... 435/290 |
| 5,066,377 A | | 11/1991 | Rosenbaum et al. ...... 204/182.8 |
| 5,154,889 A | | 10/1992 | Muraishi ....................... 422/65 |
| 5,224,536 A | * | 7/1993 | Eigen et al. ................... 165/32 |
| 5,255,976 A | * | 10/1993 | Connelly ....................... 374/31 |
| 5,410,130 A | * | 4/1995 | Braunstein ................... 219/521 |
| 5,459,300 A | * | 10/1995 | Kasman ....................... 219/433 |
| 5,525,300 A | | 6/1996 | Danssaert et al. ............ 422/99 |
| 5,601,141 A | * | 2/1997 | Gordon et al. .............. 165/263 |
| 5,851,492 A | * | 12/1998 | Blattner ....................... 422/102 |
| 6,106,784 A | * | 8/2000 | Lund et al. .................. 422/104 |

FOREIGN PATENT DOCUMENTS

| | | |
|---|---|---|
| DE | 7113471 | 7/1971 |
| DE | 3122008 | 3/1982 |
| DE | 3525860 | 1/1987 |

(List continued on next page.)

*Primary Examiner*—Jill Warden
*Assistant Examiner*—Dwayne K Handy
(74) *Attorney, Agent, or Firm*—Sidley Austin Brown & Wood, LLP

(57) ABSTRACT

The invention concerns a thermostated block for laboratory thermostats and comprising wells at a wells side to receive and make large-area contact with the parts of vials filled with sample liquids and comprising at least two heat regulating devices contact the thermostated block in thermally conducting manner to generate different temperatures at different sites of the thermostated block, said block being characterized in that the heat regulating devices are in large-area contact with adjoining zones of the contact side opposite the wells side of the thermostated block.

7 Claims, 5 Drawing Sheets

FOREIGN PATENT DOCUMENTS

Figure 1:
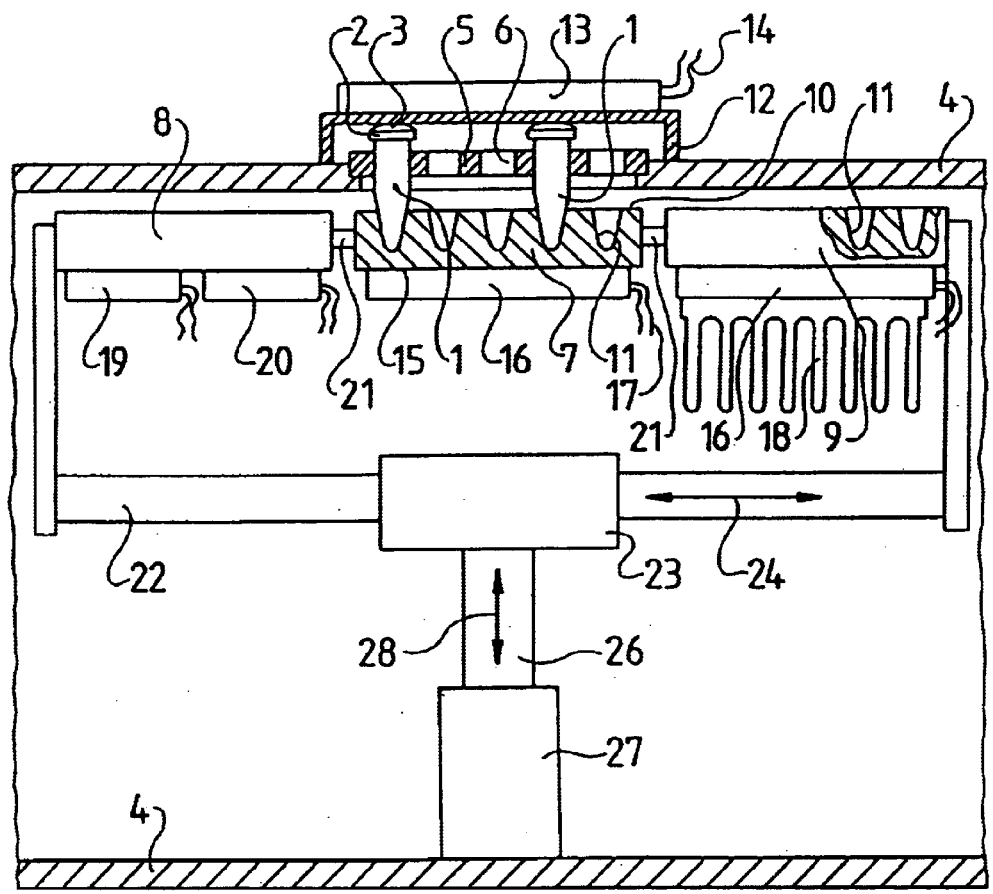

| | | |
|---|---|---|
| DE | 276547 | 2/1990 |
| DE | 4406107 | 5/1995 |
| EP | 0 504 435 | 9/1992 |
| EP | 0504435 | 9/1992 |
| EP | 0711603 | 5/1996 |
| WO | 89/12 502 | 12/1989 |
| WO | 8912502 | 12/1989 |
| WO | 9005947 | 5/1990 |
| WO | 90/05 947 | 5/1990 |
| WO | 9106369 | 5/1991 |
| WO | 91/06 369 | 5/1991 |
| WO | 92/04 979 | 4/1992 |
| WO | 9264979 | 4/1992 |
| WO | 94/01 217 | 7/1992 |
| WO | 9401217 | 7/1992 |
| WO | 9610456 | 4/1996 |
| WO | 96/10 456 | 4/1996 |

* cited by examiner

TEMPERATURE-REGULATING BLOCK WITH TEMPERATURE-REGULATING DEVICES

FIELD OF THE INVENTION

This invention relates to a thermostated block for laboratory thermostats having wells to receive and make large-area contact with segments of liquid sample filled vials and having heat regulating devices making good thermal contact with the block to generate different temperatures at different sites of the block.

BACKGROUND OF THE INVENTION

Such a thermostated block is known from U.S. Pat. No. 5,525,300. Two heat-regulating devices in thermal contact with the thermostated block at two of its opposite ends heat it at one end and cool it at the other. A thermal flow runs longitudinally between the heat regulating devices through the thermostated block so that a temperature profile is generated in the longitudinal block direction, resulting in different temperatures. A thermostated block generating such a temperature gradient allows ascertaining the optimal temperature, for instance, in the polymerase chain reaction (PCR) for a temperature stage in this process.

Controlling the temperature of the thermostated block solely at its ends, however, has a drawback. When turning the apparatus ON or when the temperature to be set in the thermostated block changes, the thermostating time delays to the desired equilibrium are substantial on account of the two-end thermostating. Furthermore, the temperature at the middle of the thermostated block may deviate from the desired temperature profile due to environmental effects.

SUMMARY OF THE INVENTION

An object of the present invention is to provide a thermostated block of the above type which allows achieving the desired temperature profile faster and without problems.

In accordance with the invention, several heat-regulating devices acting on the thermostated block make contact over a large surface with adjoining zones of the contact side. This design is remarkable in that despite the large-area contact with the heat-regulating devices uniformly supplying heat to or dissipating it from the thermostated block, the heat-regulating devices also can be used to set up a temperature gradient easily. The known end configuration of the heat regulating devices is not required for this purpose. The design of the invention offers the advantage of direct temperature control of the thermostated block over its entire surface. Environmental effects, for instance from the ambient air, are substantially excluded. Because of the large-area action across the full surface of the thermostated block, the times needed to reach the desired temperature profile also are substantially less, for instance, when the thermostated block must be switched from a temperature profile in the range of 40° C. to a temperature profile in the range of 90° C. Accordingly, it is easily feasible to change sequentially the sample temperature in a thermostated block to a different temperature level, either using a temperature gradient or alternatively using a temperature which is uniform over the entire block.

In an alternative operation, the large-area contact implemented by the heat regulating devices can be used in a very simple manner to uniformly thermostat all wells. Unlike the initially cited design of the prior art, this design of the invention does not require adding at the contact side another heat regulating device to the cooling and heating regulating devices at the ends of the thermostated block.

By providing segments at boundaries between zones of the block with different thermal impedances, the heat passing between adjacent heat-regulating devices in the thermostated block may be reduced. Effects from such heat flow between the regulating means driving the heat-regulating devices that might result in regulation oscillations are reduced thereby and the complexity of electronic regulation is decreased.

The temperature profile across the thermostated block, namely the particular temperature gradient, does not always correspond to the desired temperature profile. Deviations arise in particular at the ends of the thermostated block where the effect of the adjacent heat-regulating devices is less and thus the temperature gradient is shallower. Using such segments of different thermal conductivities allows correcting the temperature curve. In particular, a higher temperature gradient may be achieved using a higher thermal impedance, and thereby the shallow gradients at the ends may be corrected.

In an advantageous manner, the segments of the thermostated block increase in thermal impedance from its center toward its edge. As a result the temperature profile can be linearized.

The segments can be formed as are grooves which by merely reducing the local, material cross-section produce a higher thermal impedance. In contrast to the known cross-boreholes found for such purposes in the initially cited design of the state of the art, the invention's configuration offers easier manufacture and a more advantageous geometry between wells in the form of recesses.

Dividing the contact side of the block longitudinally and transversely into zones making contact with separate heat regulating devices is also advantageous. The heat regulating devices distributed across the surface may be operated in a variety of ways. Laterally adjacent heat-regulating devices may be operated to be identically thermostating so that a temperature gradient is set up in the longitudinal or in the transverse direction of the thermostated block. Illustratively, a gradient may be set up in a thermostated block at different temperature levels in different directions. Also, the heat-regulating devices each may be operated differently so that a temperature gradient may be set up as well in the x-direction as in the y-direction, for instance with different temperature gradients in the two directions.

Two different types of laboratory vials may be used without having to convert the laboratory thermostats. Even mixed outfitting is possible. The large number of closely adjoining recesses in the form of wells allows lowering the mass of the thermostated block. As a result the heat capacity of the block is lowered and the temperature may be raised more rapidly to the desired temperature. Moreover it is also possible to make the thermostated block thinner toward its wells side whereby the heat between the heat-regulating devices preferably follows a path through a plate-region of the thermostated block adjacent to the contact side, and as a result the desired temperature can be set very accurately and uniformly. Thereby, the wells of one type are made to match a predetermined grid arrangement of vials. Hence, vials also may be used which illustratively are integrated into a continuous plate configuration. The desired thinning of the upper part of the thermostated block situated toward the receiving side may be enhanced by additional holes between the wells. A continuous plate of the thermostated block, running continuously underneath the wells and holes, increases the uniformity of the temperature setting. Segments having higher thermal impedances as are present in the initially cited conventional design in the form of boreholes may be used to correct the desired temperature profile. Advantageously such segments are in the form for instance of grooves running from the contact side and illustratively meandering between the wells and the holes.

The block together with another heat regulating device can be made displaceable relative to a plate holder supporting the vials and can be exchangeably moved to a position of alignment of the wells relative to the vials. As in the known design, they make it possible to subject the containers sequentially to various thermostated blocks thermostated at different levels and each having either a temperature gradient or a temperature constant across its surface. To allow sideways motion, the thermostated blocks may be mounted in a laterally displaceable carriage. They also may be mounted in a rotor for that purpose, the rotor illustratively rotating like a lazy Susan in a plane parallel to the holding means. Preferably, they are rotated together with a rotor about a shaft parallel to the holding means to allow especial compactness. The blocks may be displaced to move away from the rotor, or preferably the rotor is moved to effect separation as a whole.

The invention is shown illustratively and schematically in the drawings.

Figure 2:
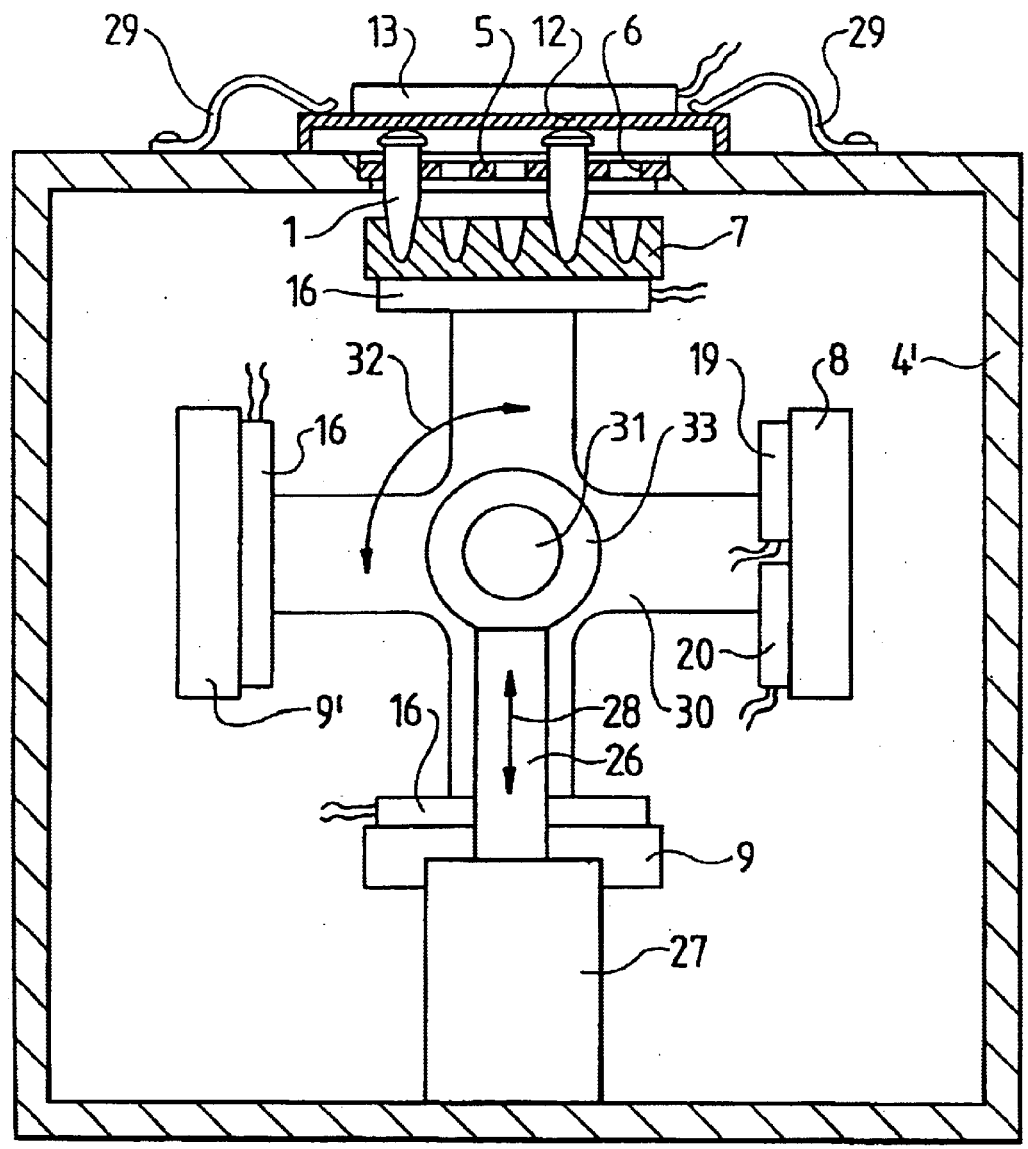
Figure 3:
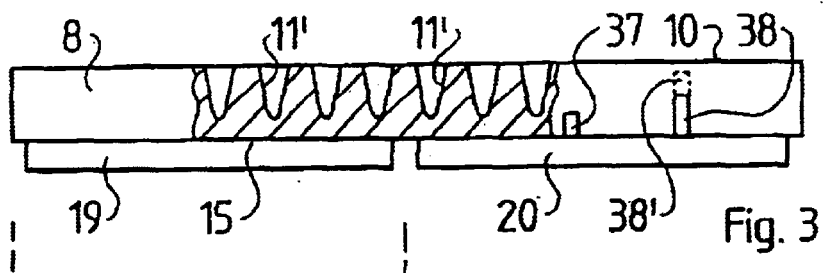
Figure 3A:
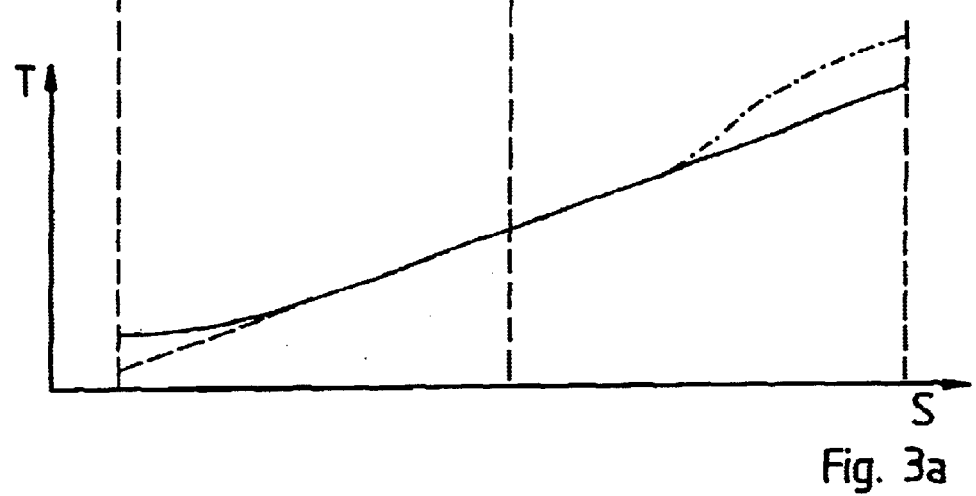
Figure 4:
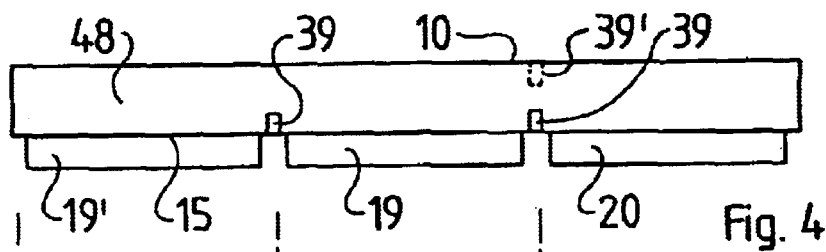
Figure 4A:
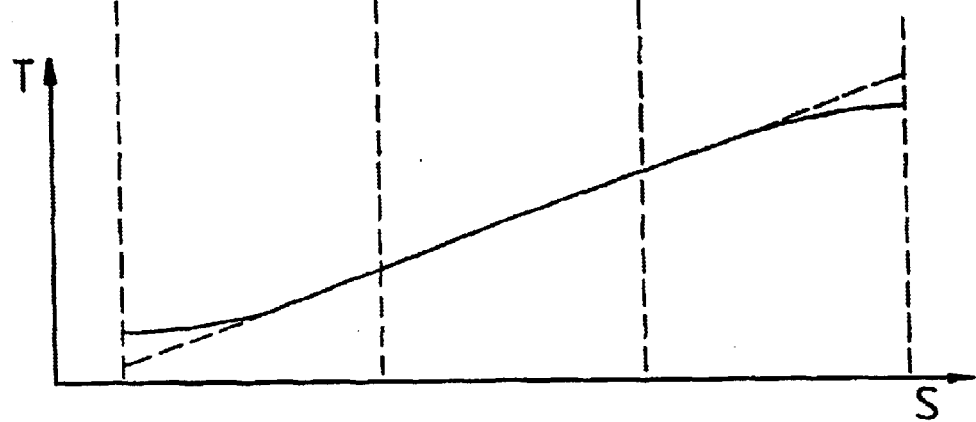
Figure 5:
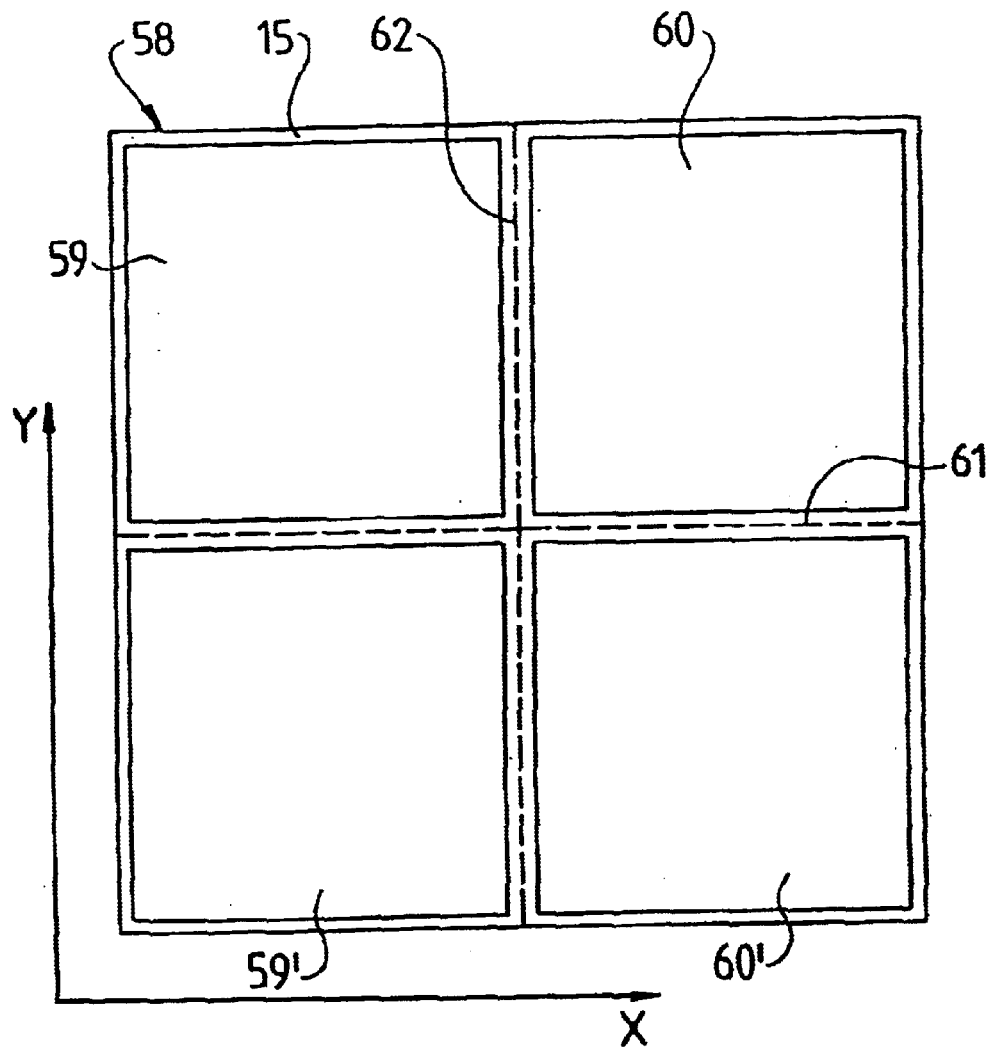
Figure 6:
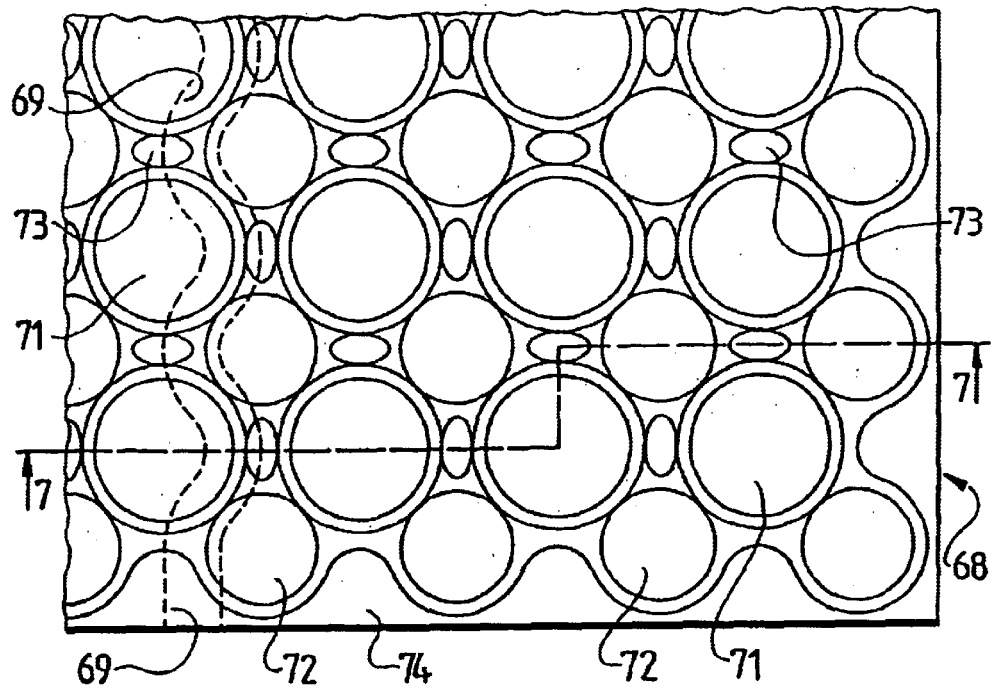
Figure 7:
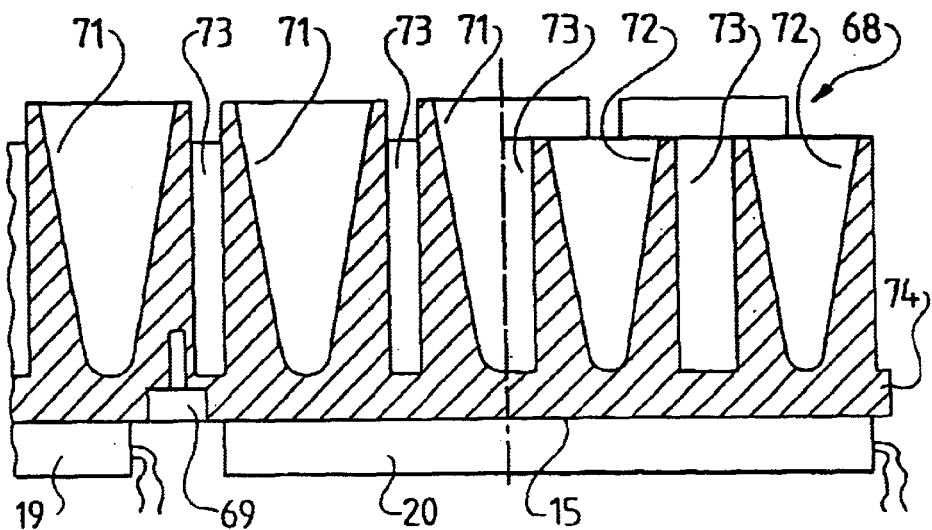

FIG. 1 is a cross-section of a laboratory thermostat according to the invention with a block AC drive of a first embodiment, FIG. 2 is a cross-section of a laboratory thermostat with a second embodiment of a block-change drive, FIG. 3 is a thermostated block to generate a first embodiment of a temperature gradient, FIG. 3a is a graph showing the temperature gradient of the block of FIG. 3, FIG. 4 is a thermostated block to generate a second embodiment of a temperature gradient, FIG. 4a is a graph showing the temperature gradient of the block of FIG. 4, FIG. 5 is a side elevation from the contacting side showing a quadrant configuration of four heat-regulating devices, FIG. 6 is a top plan view of a thermostated block corresponding to that of FIG. 4 with a detailed view of the wells, and FIG. 7 is a section along line 7—7 of FIG. 6.

FIG. 1 shows a laboratory thermostat which is especially appropriate for the PCR process. Sample liquids, for instance mixtures of reactions, are to be sequentially set to different temperatures.

For that purpose, the sample liquids are present in vials 1 which in the embodiment shown are commercial thin-walled plastic reaction vials. Each vial comprises a cylindrical part which, as shown in FIG. 1, tapers conically at its lower end region receiving the sample liquid. The upper edge comprises a collar 2 and an elastically deforming lid 3 closing vial 1.

The laboratory thermostat shown comprises an enclosing housing 4 receiving at its top side a perforated plate acting as a holder 5 with holes 6 keeping the vials 1 in place and securing the vials at their collars 2 against dropping out of the plate.

A thermostated block 7 is mounted underneath the holding plate 5 and comprises at its upper side 10, herein called the wells side, wells 11 having shapes corresponding to the shapes of the lower ends of vials 1. The configuration of the wells 11 in the surface of the wells side 10 of the block 7 corresponds to the configuration of the holes 6 in the holding plate 5. In the shown position of thermostated block 7 underneath holding plate 5, wherein wells 11 are aligned with holes 6, the lower ends of all vials 1 in holding plate 5 make surface contact with block 7 when the vials enter wells 11.

To assure that there is good thermally conducting surface contact between vials 1 and wells 11 of block 7, a platecover 12 covering holding plate 5 is mounted over plate 5 and presses against the elastic lids of vials 1. In order to reliably thermostat the sample liquids in vials 1 and to preclude condensation on vial lids 3, the plate cover 12 is raised to an appropriate temperature using a heat-regulating device 13, for instance a Peltier element having leads 14.

At the contacting side 15, block 7 makes contact, opposite its wells side 10, with a heat regulating device 16 which, illustratively, may be a Peltier element electrically powered through its leads 17. A Peltier element is especially well suited for such purposes because it can be used to heat or cool, depending on need.

Heat regulating device 16 allows bringing the block 7 to a desired temperature. Preferably a temperature sensor, provided for that purpose at a suitable site of the block 7, controls heat regulating device 16 by means of an electronic regulator to keep the temperature in block 7 constant at a suitable level.

If, as shown, surface contact is made between block 7 and vials 1 through the block's wells 11, then the sample liquid in the vials very rapidly and with very high accuracy assumes the temperature of the block 7, i.e. the desired temperature of reaction.

In the embodiment shown, the laboratory thermostat comprises two further blocks 8 and 9 corresponding in the design of their wells to the wells 11 of the block 7 already discussed. Heat regulating blocks 8 and 9 also are fitted with heat regulating devices, in the case of block 9 with a heat regulating device 16 and in that of the thermostated block 8 with two adjoining heat regulating devices 19 and 20 which can be operated in parallel at the same temperature but also, as elucidated further below, at different temperatures. Heat regulating device 16 under thermostated block 9 is fitted with a cooling body 18 which also may be present at the other heat regulating devices and which in that event offers the advantage, if the heat regulating device is a Peltier element, that heat must be dissipated or received on its surface away from the heat regulating block.

The configuration of wells 11 in all three blocks 7, 8 and 9 is identical. Accordingly, the blocks can be made to selectively act on vials 1 in holding plate 5.

For that purpose a block-changeover drive is provided. Blocks 7, 8 and 9 are rigidly connected to each other by co-planar braces 21 to form a laterally displaceable carriage that is fitted with a push rod 22 and is longitudinally displaceable in the direction of the arrow 24 inside a slide guide 23. The lateral drive so formed for thermostated blocks 7, 8 and 9 is height-adjustable as a unit by means of a spacing drive means.

To implement the spacing motion, slide guide 23 is fixed to a push rod 26 resting in a height-adjustable manner in the direction of the arrow 28 in a slide guide 27.

When the thermostated blocks are in the position shown in FIG. 1, with thermostated block 7 engaging vials 1, block 7 may be disengaged from the vials by descent of rod 26 into the slide guide 27. Then, by adjusting push rod 22 of the lateral drive, one of the other two blocks can be moved in a position aligned with and underneath holding plate 5 and, upon ascent of rod 26 in slide guide 27, it may be made to act on vials 1.

In this manner, vials 1 seated in holding plate 5 can be alternatingly moved to make thermal contact with the heat regulating blocks 7, 8 or 9. These blocks can be kept thermostated at different temperatures. Therefore, the vials 1 can be made to rapidly assume different, highly accurate temperatures as especially desirable for PCR purposes.

In the same manner as the holes 6 in holding plate 5, wells 11 in the thermostated blocks 7, 8 and 9 may be configured in an appropriate manner, for instance in rows and columns. The vials can be exchanged upon removing plate cover 12. Illustratively, they may exchanged in a labor-saving manner together with the holding plate 5 which, for such a purpose, must be made replaceable in housing 4.

In lieu of the three shown thermostated blocks 7, 8 and 9, another number of blocks may also be used in the shown linear carriage configuration depending on the desired number of temperature steps.

Moreover, the configuration of lateral drive and spacing drive may be altered. Illustratively, the blocks can be linked by individual spacing drives to one lateral drive.

The blocks may be driven manually to exchange them underneath the vials 1 or preferably for instance by computer-controlled motor-drives which, in a manner not shown, drive push rod 22 relative to its slide guide 23 and also drive push rod 26 relative to its slide guide 27. In this manner it is possible to program-control a heat regulating cycle of a given sequence.

In lieu of the block drive means shown in FIG. 1, wherein the side drive element is in the form of the slide carriage with slide guide 22, 23, said side drive element for instance also may be a lazy Susan drive. In that instance, the shown blocks 7, 8 and 9 must be mounted co-planarly parallel to the holding plate 5 and be pivotable about an axis of rotation perpendicular thereto.

Another advantageous embodiment of the block-changeover drive means is shown in FIG. 2. The design elements correspond to those of FIG. 1. As far as possible, congruent components are identically referenced.

Holding plate 5 seating vials 1 is in the top side of a somewhat differently shaped housing 4'. It is again covered by a plate cover 12 assuring pressure and heat regulating of the vials from above. FIG. 2 additionally shows disengageable clamping means 29 which also may be used in the embodiment of FIG. 1 and which secure the plate cover 12 in its shown position.

In the embodiment of FIG. 2, the laboratory thermostat comprises the three thermostated blocks 7, 8 and 9 of FIG. 1 and an additional thermostated block 9' which is designed correspondingly. These thermostated blocks correspond to the embodiment of FIG. 1 including the associated heat regulating devices. In its shown position, thermostated block 7 engages vials 1 while being aligned underneath holding plate 5.

The drive means for the lateral displacement of the thermostated blocks is basically different from the embodiment of FIG. 1.

Blocks 7, 8, 9 and 9' are affixed at 90° angularly separated positions to a rotor 30 which is supported for bidirectional rotation about a shaft 31, in the direction of the arrow 32, at the head 33 of push rod 26 which is longitudinally displaceable according to FIG. 1 in the direction of arrow 28 in slide guide 27.

In order to change the thermostated block underneath holding plate 5, first push rod 26 together with rotor 30 are displaced downward until the thermostated block just barely engaging vials 1 becomes disengaged from them. Thereupon, rotor 30 is rotated by a multiple of 90° in order to move another thermostated block into alignment with and underneath holding plate 5. By raising push rod 26, the new plate comes into contact with vials 1. In this design too, motor drives, not shown, may be provided which illustratively are computer-controlled to assure fully automatic operation.

A comparison of FIGS. 1 and 2 shows that the embodiment of FIG. 2 with its rotating drive of the thermostated blocks is more compact.

FIG. 3 is a side view of two heat regulating devices 19 and 20 of thermostated block 8 of FIGS. 1 and 2. The wells 11', having the shapes of wells receiving the vials, in this case are somewhat smaller and more numerous. The wells 11' may be arrayed in rows and columns at the wells side 10. They serve to seat a larger number of vials to be thermostated.

The heat regulating devices 19 and 20 resting against block 8 at contact side 15 preferably are Peltier elements fitted with leads, not shown in FIG. 3, for electrical power. Thereby arbitrary temperatures may be set by heating or cooling. Heat regulating devices 19 and 20, however, also may be in the form of heat exchangers with liquids passing therethrough and illustratively supplied through hoses.

Heat regulating devices 19 and 20 may be brought to identical temperatures or to different ones. Temperature sensors, not shown, in the block above the heat regulating devices may be connected with a regulator controlling the heat dissipation or input by the heat regulating devices.

Heat regulating devices 19 and 20 shown in FIG. 3 each rest against approximately one half of the contact side 15 with the contact face of each heat regulating device 19, 20 being in a full area contact with the contact side 15, i.e., with the entire faces of the devices (19, 20) contacting the contact side. Good thermal contact may be implemented by bonding or other affixation. If heat regulating devices 19 and 20 are brought to different temperatures, and in the present case the heat regulating device 20 being at the higher one, a temperature function over the length of the thermostated block 8 shown in FIG. 3a results. Heat regulating device 20 constantly supplies heat to the thermostated block 8 while the heat regulating device 19 dissipates heat from said thermostated block by cooling it. Therefore there is a heat flow through the thermostated block 8 between heat regulating devices 20 and 19.

FIG. 3a shows the temperature function T over the range S with a linear temperature function at the center. At the left end, that is above the heat regulating device 19, the temperature curve becomes shallower because the heating effect of the heat regulating device 20 drops ever more toward the left end of the thermostated block.

On the right side, that is above the heat regulating device 20, the temperature function is linear as far as the end of the thermostated block as shown in FIG. 3a. This feature is assured by two grooves 37 and 38 running parallel to the interface between the zones of heat regulating devices 19 and 20 contacting contact side 15. These grooves reduce locally the material cross-section of the thermostated block 8 and assure a local increase in thermal impedance of the otherwise thermally well-conducting, illustratively metallic block, in the direction of heat flow in this block from the heating heat regulating device 20 to the cooling heat regulating device 19. The temperature gradient of the temperature function shown in FIG. 3a being proportional to the product of heat flow and thermal impedance, the shape of the temperature function can be controlled by locally changing the thermal impedance and in particular, as shown in FIG. 3a, it can be linearized. Advantageously in this respect the depth of the grooves 37 and 38 will differ, that is, they entail different local, material cross-sectional reductions of the block. The depths and configurations of the grooves 37 and 38 of FIG. 3 are merely illustrative. The precise depths, positions and number of the grooves can be ascertained for instance empirically.

FIG. 3a shows that the temperature function becomes shallower at the left end of thermostated block 8. At the right side, that is above heat regulating device 20, such a shallow slope is compensated-for by providing grooves 37 and 38. As shown in FIG. 3, groove 38 is deeper than groove 37 because it is nearer to the right block edge, that is it is in a zone wherein the heat flow from the heat regulating device 20 to the heat regulating device 19 is less than where the groove 37 is located. To generate the same temperature gradient at the position of the groove 38, a higher thermal impedance, that is a deeper groove, is required. If now groove 38 is deepened further, as indicated in dashed lines at 38', the temperature profile in this zone may be raised further as indicated in dash-dot lines in FIG. 3a.

FIG. 4 shows a thermostated block 4 corresponding to that of FIG. 3 with three heat regulating devices 19', 19 and 20. If the heat regulating device 20 is heating and the heat regulating device 19' is cooling, the temperature function shown in FIG. 4a is obtained. At the ends of the function, that is above the heat regulating devices 19' and 20, the function becomes shallower because such grooves above the heat regulating devices as grooves 37 and 38 (FIG. 3) are missing.

A linear temperature gradient is achieved across the middle heat regulating device 19. The middle heat regulating device 19 can be operated at a middle temperature or it optionally may be shut off. It is needed to prevent any deviation of the temperature function at the center of the block and in particular it is needed when the temperature function must be rapidly shifted to another level. It is also needed when alternatively all the block must be brought to the same temperature.

The temperatures must be regulated to achieve the required accurate temperature setting in the thermostating block 48. For that purpose the heat regulating devices 19', 19 and 20 each are controlled in their own control loop by temperature sensors, not shown, in the block above the individual heat regulating devices. Heat exchange between the control loops takes place by heat flow in the block between the heat regulating devices. This feature entails interaction among the control loops and substantially interfering regulation oscillations may arise.

These regulation oscillations may be minimized by reducing the heat flow between the heat regulating devices. Therefore the embodiment shown in FIG. 4 comprises grooves 39 increasing thermal impedance between the heat regulating devices at the boundaries between the areas of the contact side 15 that are fitted with heat regulating devices 19', 19 and 20.

As further shown in dashed lines for groove 39' in FIG. 4, grooves 39 also may be inserted from the top, that is in the wells side 10. Grooves 37 and 38 of FIG. 3 also may be inserted alternatively from the top, that is from the wells side 10, into the block.

FIGS. 3 and 4 show grooves 37, 38 and 39 designed to hamper for different reasons the heat flow in the thermo- stated block by reducing the local, material block cross-section and thereby reducing the thermal conductivity at such sites, in other words, increasing the thermal impedance. The shown grooves also may be replaced in other ways to locally change the block's thermal conductivity. The grooves may be replaced by segments present in another manner in the thermostated block and having a different thermal conductivity, i.e. another thermal impedance than the remaining block zones. Illustratively such segments may be created by splitting the block at such a site and inserting (sandwiching) a material of higher thermal impedance. These segments, just as the grooves shown in FIGS. 3 and 4, may run in lines through the block, but preferably in a straight line transversely to the heat flow between two block edges. Thus the grooves shown in FIGS. 3 and 4 preferably run transversely to block 8 or 48, that is, perpendicular to the plane of the drawing, and through the entire block.

Thermostated blocks 8 and 48 shown in FIGS. 3 and 4 are fitted with two heat regulating devices 19 and 20 or three heat regulating devices 19', 19 and 20 each extending over the full width of the block. Accordingly, a temperature gradient can be set up in this block only in the longitudinal direction as shown by the temperature functions of FIGS. 3a and 4a, that is from left to right in the drawings.

FIG. 5 shows an embodiment of a thermostated block 58 in which the contact side 15 having zone boundaries 61 and 62 is divided into four quadrant zones with heat regulating devices 59, 60, 59' and 60'. If heat regulating devices 59 and 59' are operated in the same manner, for instance in the cooling mode, and if heat regulating devices 60 and 60' are operated at the same temperature, then a temperature gradient in the direction of the x-axis will be set up in thermostated block 58. If heat regulating devices 59 and 60 are operated at the same temperature and heat regulating devices 59' and 60' also are operated at the same temperature, then a temperature gradient will be set up in the direction perpendicular thereto, that is in the y-direction. If all heat regulating devices are operated at the same temperature, the full thermostated block 58 will be at a uniform temperature.

The possibility of generating temperature gradients alternatingly in the x- or y-directions makes possible an embodiment variation wherein thermostated block 58 is sequentially operated at two different temperature levels, for instance at a level of 30° C. and at a level of 60° C. The precisely optimal temperature at both temperature levels is now assumed being sought. This result can be achieved in one pass, first the thermostated block being operated with a gradient at the 30° C. level in the x-direction and illustratively temperatures of 28, 29, 30, 31, 32° C. being generated. Next the thermostated block is raised to the 60° C. level with a temperature gradient in the y-direction, different temperatures for instance of 58, 59, 60, 61 and 62° C. being generated. If the thermostated block is loaded across its surface into regular rows (x direction) and columns (y direction) with samples to be thermostated, then these samples may thereupon be analyzed and a determination thus can be made which ones were optimally thermostated. The optimal temperature was present at both temperature levels.

Another possible embodiment is significant wherein all four heat regulating devices are simultaneously kept at different temperatures. A complex temperature mosaic with different temperatures in both x- and y-directions may thus be produced. Illustratively, a steeper temperature gradient may be set in the x-direction and a shallower one in the y-direction. If at the wells side of the thermostated block 58 the wells are configured in rows (x-direction) and columns (y-direction), then illustratively temperature differentials of 1° C. can be set between the rows and temperature differentials of 1/10° C. inside the rows between the columns. Accordingly temperature differentials for instance of 10° C. with a resolution of 1/10° C. may be set.

FIGS. 6 and 7 are respectively a top view of the wells side and a cross-section of a thermostated block 68 corresponding in its basic design to the thermostated block 8 already discussed, namely being in contact at its contact side 15 with two heat regulating devices 19 and 20.

Two different kinds of wells 71 and 72 of different depths are formed at the wells side into said block.

As shown by FIG. 6, the two sorts of wells 71 and 72 nest in each other in an orthogonal array and are configured in such a way that one well 72 of the second sort lies between four wells 71 of the first sort. Consequently and as shown in FIG. 7, a filigree block design is obtained having a much reduced local, material cross-section in the upper block zone, that is toward its wells side. Moreover, oval holes 73 are additionally provided between wells 71 and 72 and are each located centrally between two large wells 71 and two small wells 72 as indicated in FIG. 6. Those holes additionally reduce the material at the upper side of thermostated block 70. Thereby heat conduction is less between heat regulating devices 20 and 19 at the block's upper thickness reduced by the wells 71, 72 and the holes 73 than it is in the lower part of the continuous plate 74 running underneath all wells 71, 72 and holes 73.

As shown by FIG. 6, the volume of the thermostated block 68 in this design is substantially reduced at its upper thick zone away from contact side 15. Consequently, the heat capacity of the thermostated block is much decreased. This feature allows very rapidly bringing the thermostated block to a desired temperature, for instance heating or cooling it from one temperature level to another. As a result, the laboratory thermostat shown in FIG. 1 or FIG. 2 can thereby sequentially operate several temperature levels in one of the shown thermostated blocks. Illustratively, especially close temperature levels may be operated in one thermostated block while another thermostated block is used for a more remote temperature level. As regards the conventional three temperature levels of the PCR procedure, illustratively two temperature levels may be operated in a first block and one in a second block. The large-area contact shown in the Figures between the thermostated block and the heat regulating devices serving to quickly heat or cool also is helpful in that respect.

The very low-mass design of thermostated block 68 shown in FIGS. 6 and 7 not only assures a much reduced heat capacity of the block but also low thermal conductivity, i.e. a high thermal impedance of the thermostated block in the direction of heat flow between heat regulating devices 20 and 19. In order to achieve a desired temperature profile or a temperature gradient such as is illustratively shown in FIGS. 3a and 4a, only a slight heat flow is needed on account of the high thermal impedance. Therefore heat regulating devices 19 and 20 may be elements drawing less power.

The thermostated block 68 shown in FIGS. 6 and 7 comprises a groove 69 with the function of thermally decoupling heat regulating devices 20 and 19 from each other as was elucidated above in relation to FIG. 4a. As shown in cross-section in FIG. 7, groove 69 is stepped in order to reach as deeply as possible between wells 71, 72 and holes 73 without, however, touching them. As shown in dashed lines in FIG. 6, groove 69 for that purpose meanders between the wells and the holes. Illustratively, the thermostated block 68 may be shape-cast or be made with a numerically controlled milling machine, for instance being aluminum.

Similarly to groove 39 shown in dashed lines in FIG. 4, groove 69 of the embodiment of FIGS. 6 and 7 may be inserted from the wells side, that is in FIG. 7 from the top, into thermostated block 68. Groove 68 illustratively may run transversely through wells 71, 72 and holes 73 or it may circumvent them in meandering manner, for instance in the form of a very narrow and deep slit.

What is claimed is:

1. A thermostated block for laboratory thermostats, comprising:

a body of thermally conductive material and having a wells side with a plurality of wells for receiving a plurality of sample liquid-containing vials provided between opposite end sides of the body, and a contact side extending opposite the wells side and parallel thereto; and at least two heat regulating devices spaced from each other and operable at different temperatures for providing a temperature gradient in one direction across the thermostated block and arranged at the contact side of the body in an area contact with the contact side;

wherein at least one of the at least two heat regulating devices is opposed by at least two wells arranged one behind another in the direction of the temperature gradient;

wherein the thermostated block comprises at least two heat regulating devices arranged behind one another in a direction transverse to the one direction for providing a temperature gradient in the transverse direction and operable at one of same temperatures and different temperatures.

2. A thermostated block for laboratory thermostats comprising:

a body of thermally conductive material and having a wells side with a plurality of wells for receiving a plurality of sample liquid-containing vials provided between opposite end sides of the body, and a contact side extending opposite the wells side and parallel thereto; and at least two heat regulating devices spaced from each other and operable at different temperatures for providing a temperature gradient in one direction across the tempering block and arranged at the contact side of the body in an area contact with the contact side;

wherein at least half of a number of all of the wells provided in the wells side are located opposite the at least two heat regulating devices.

3. A thermostated block according to claim 2, wherein the at least half of a number of wells provided in the wells side are arranged one after another in the direction of the temperature gradient.

4. A thermostated block for laboratory thermostats comprising:

a body of thermally conductive material and having a wells side with a plurality of wells for receiving a plurality of sample liquid-containing vials provided between opposite end sides of the body, and a contact side extending opposite the wells side and parallel thereto; and at least two heat regulating devices spaced from each other and operable at different temperatures for providing a temperature gradient in one direction across the thermostated block and arranged at the contact side of the body in an area contact with the contact side, wherein the at least two heat regulating devices extend at least over half of a length of the contact side measured in the direction of the temperature gradient.

wherein the thermostated block comprises at least two heat regulating devices arranged behind one another in a direction transverse to the one direction for providing a temperature gradient in the transverse direction and operable at one of same temperatures and different temperatures.

5. A thermostated block according to claim 4, wherein a contact area of the area contact of the at least two heat regulating devices with the contact side amounts to at least a half of an entire surface area of the contact side.

6. A thermostated block for laboratory thermostats, comprising:

- a body of thermally conductive material and having a wells side with a plurality of wells for receiving a plurality of sample liquid-containing vials provided between opposite end sides of the body, and a contact side extending opposite the wells side and parallel thereto; and
- at least two heat regulating devices spaced from each other for providing a temperature gradient in one direction across the thermostated block and arranged at the contact side of the body in an area contact with the contact side;
  - wherein the at least two heat regulating devices are arranged one behind another in the direction of the temperature gradient, and operable at one of same temperatures and different temperatures, and
  - wherein the thermostated block comprises at least two heat regulating devices arranged one behind another in a direction transverse to the one direction for providing a temperature gradient in the transverse direction and operable at one of same temperatures and different temperatures.

7. A thermostated block for laboratory thermostats, comprising:

- a body of thermally conductive material and having a wells side with a plurality of wells for receiving a plurality of sample liquid-containing vials provided between opposite end sides of the body, and a contact side extending opposite the wells side and parallel thereto; and
- at least two heat regulating devices spaced from each other and operable at one of different temperatures and same temperatures for providing a temperature gradient in one direction across the tempering block and arranged at the contact side of the body in an area contact with the contact side;
  - wherein at least one of the at least two heat regulating devices is opposed by at least two wells arranged one behind another in the direction of the temperature gradient;
  - wherein the thermostated block comprises at least two heat regulating devices arranged behind one another in a direction transverse to the one direction for providing a temperature gradient in the transverse direction and operable at one of same temperatures and different temperatures.

* * * * *

UNITED STATES PATENT AND TRADEMARK OFFICE
CERTIFICATE OF CORRECTION

PATENT NO. : 6,767,512 B1
APPLICATION NO. : 09/101124
DATED : July 27, 2004
INVENTOR(S) : Werner Lutz et al.

It is certified that error appears in the above-identified patent and that said Letters Patent is hereby corrected as shown below:

In Claim 2 at Column 10, line 48, please change "tempering" to -- thermostated --.

In Claim 7 at Column 12, line 19, please change "tempering" to -- thermostated --.

Signed and Sealed this

Thirtieth Day of October, 2007

JON W. DUDAS
*Director of the United States Patent and Trademark Office*